United States Patent [19]

Holmes et al.

[11] Patent Number: 4,628,127
[45] Date of Patent: Dec. 9, 1986

[54] HETEROGENEOUS CATALYTIC ALKYLATION

[75] Inventors: Silas W. Holmes, Columbia; Edward A. Burt; Dixie E. Goins, both of Orangeburg, all of S.C.

[73] Assignee: Ethyl Corporation, Richmond, Va.

[21] Appl. No.: 748,744

[22] Filed: Jun. 25, 1985

[51] Int. Cl.$^4$ ...................... C07C 37/14; C07C 39/06
[52] U.S. Cl. .................... 568/781; 568/743; 568/780; 568/784; 568/785
[58] Field of Search ............... 568/781, 789, 780, 794, 568/784, 785, 788, 783, 743; 502/159

[56] References Cited

U.S. PATENT DOCUMENTS

| | | | |
|---|---|---|---|
| 2,442,878 | 6/1948 | Schmerling et al. | 568/794 |
| 2,831,898 | 4/1958 | Ecke | 568/789 |
| 3,037,052 | 5/1962 | Bortnick | 568/789 |
| 3,091,646 | 5/1963 | Leston | 568/784 |
| 3,355,504 | 11/1967 | Coffield et al. | 568/794 |
| 3,422,157 | 1/1969 | Kaufman et al. | 568/784 |
| 3,426,358 | 2/1969 | Schlichting et al. | 568/794 |
| 3,798,281 | 5/1974 | Wang | 502/159 |
| 3,843,606 | 10/1974 | Van Slrge | 502/159 |
| 3,933,927 | 1/1976 | Goddard | 568/784 |
| 4,198,531 | 4/1980 | Merger et al. | 568/789 |
| 4,398,048 | 8/1983 | Firth | 568/790 |
| 4,461,916 | 7/1984 | Alfs | 568/785 |
| 4,476,329 | 10/1984 | Chamber et al. | 568/780 |

FOREIGN PATENT DOCUMENTS

| | | | |
|---|---|---|---|
| 59-130823 | 6/1984 | Japan | 568/789 |
| 455742 | 1/1975 | U.S.S.R. | 502/159 |
| 0789483 | 12/1980 | U.S.S.R. | 568/804 |

Primary Examiner—Werren B. Lone
Attorney, Agent, or Firm—Donald L. Johnson; John F. Sieberth; Edward F. Sherer

[57] ABSTRACT

A process for producing 2,4-di-substituted phenols wherein an olefin is reacted with phenol in the presence of a heterogeneous catalyst comprising an aluminum phenoxide bonded to an acidic solid polymeric resin to preferably form 2,4-di-substituted phenol. A process for preparing a heterogeneous catalyst and a heterogeneous catalyst having the structure $$(\text{Resin}-\text{A}-)_m \text{Al}(-\text{OC}_6\text{R}_5)_n \qquad (11)$$

wherein Resin is a solid polymeric resin having acidic functional groups A, m is 1 or 2, n is 2 or 3 and the R are independently selected from H, alkyl, cycloalkyl, and aralkyl. Preferably, a styrene-divinylbenzene polymeric resin of a macroreticular structure is used for the alkylation process and A is —SO$_3$—.

33 Claims, No Drawings

HETEROGENEOUS CATALYTIC ALKYLATION

BACKGROUND OF THE INVENTION

The present invention relates to alkylation of phenols and to polymeric resins. In particular, the present invention relates to processes for the alkylation of phenols using an aluminum alkoxide catalyst.

DESCRIPTION OF THE PRIOR ART

In the past, phenols have been alkylated using aluminum alkoxide catalysts in a homogeneous phase wherein an aluminum alkyl is reacted with a phenol to form an aluminum phenoxide catalyst for alkylating a phenol. Such processes include methods for preparation of commercially valuable antioxidants. In such processes, the aluminum which forms an aluminum phenoxide catalyst must be hydrolyzed from the solution to become a phenol-bearing waste stream which significantly detracts from the economics of production of such alkylated phenols.

CROSS REFERENCE TO RELATED APPLICATION

The invention of the present application is related to co-pending application Ser. No. 748,733, filed June 15, 1985, commonly assigned.

SUMMARY OF THE INVENTION

The present invention is directed to the production of 2,4-di-substituted phenols which have advantageous antioxidant properties in themselves and which may be used to form phosphite antioxidants and other compounds having additional utilities. The invention is a process for making 2,4-di-substituted phenols by reacting an olefin and a suitable phenol starting material in the presence of a heterogeneous catalyst comprising an aluminum phenoxide bonded to an acidic solid polymeric resin (one having acidic functional groups) so as to form 2,4-di-substituted phenols. The heterogeneous catalyst is formed by (1) reaction of an aluminum phenoxide or (2) reaction of an aluminum alkyl or other aluminum compound with the resin followed by reaction with a phenol. Advantageously, the heterogeneous catalyst of the invention is easily recovered and readily recycled for repeated reactions and gives a high yield of 2,4-di-substituted phenolic product for numerous reaction sequences. The invention also includes a process for preparing the catalyst by reacting the pendant acidic groups (preferably SO₃H groups) of an acidic resin with an aluminum phenoxide or, alternatively, with an aluminum alkyl or other aluminum compound followed by a reaction with a phenol, preferably phenol.

The invention is also the heterogeneous catalyst per se which comprises an aluminum phenoxide bonded to a solid polymeric resin having acidic functional groups.

DESCRIPTION OF THE PREFERRED EMBODIMENTS

A preferred embodiment of the present invention is a process for producing 2,4-di-substituted phenols comprising reacting an olefin and a phenol of structure I:

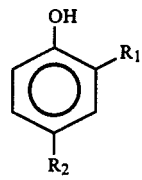

wherein one of $R_1$ and $R_2$ is H and the other is independently selected from the group consisting of H, alkyl of from 1–12 carbon atoms, cycloalkyl of from 5–12 carbon atoms, and aralkyl of from 7–12 carbon atoms; said reacting being carried out in the presence of a heterogeneous catalyst comprising an aluminum phenoxide bonded to a solid polymeric resin having acidic functional groups; and forming as the major product 2,4-disubstituted phenol. In a more preferred embodiment of the invention, both $R_1$ and $R_2$ are H or one of $R_1$ and $R_2$ is alkyl of from 1 to 12 carbon atoms, more preferably sec-alkyl or tert-alkyl, still more preferably sec-butyl, isobutyl, or tert-butyl. Alternatively, $R_1$ or $R_2$ may be methyl in still another embodiment of the invention.

In general, the heterogeneously catalyzed process of the present invention is usable with any of the various phenols which were heretofore catalyzed by homogeneous catalyst systems.

The acid resin may be any of the various resins commercially available including styrene-divinylbenzene resin and the like which have a pendant acid group, e.g. —SO₃H. The sulfonic acid styrene divinylbenzene resin is preferred for the process of the invention. The resins may be of the ion exchange type, the adsorber type, or another type.

The terms "a phenol" or "phenols" when used herein refers to the generic family of phenols which includes the compound phenol, C₆H₅OH as well as substituted phenols. Thus, phenols usable as starting material for the process of the present invention include those phenols not already 2,4-disubstituted. Suitable starting materials for the invention are the compound phenol (C₆H₅OH), ortho-tert-butylphenol, para-tert-butylphenol, ortho-cresol, para-cresol, ortho-ethylphenol, para-ethylphenol, ortho-isopropylphenol, para-isopropylphenol, ortho-sec-butylphenol, 2,6-di-tert-butylphenol, 2,6-dimethylphenol, ortho-octylphenol, ortho-hexylphenol, ortho-pentylphenol, ortho-n-butylphenol, ortho-tert-amylphenol, ortho-cyclo-hexylphenol, ortho-benzylphenol, 2,6-dibenzylphenol, 2-methyl-6-tert-butylphenol, 2-isopropyl-6-sec-butylphenol, 2-phenyl-6-benzylphenol, 4-benzylphenol, 4-n-butylphenol, and others. Phenol and ortho-alkylphenols are the most highly preferred reactant phenols. The phenols may optionally be halo-substituted with, e.g. chloro or bromo substituents. Also, the phenols may be meta-substituted.

A preferred class of phenols includes the compound phenol and various lower alkyl substituted phenols not already 2,4-di-substituted. These include ortho-tert-butylphenol, ortho-isorpopylphenol, ortho-sec-butylphenol, and the like. The compound phenol, ortho-tert-butylphenol, and ortho-sec-butylphenol are highly preferred.

In one embodiment, phenol is reacted with an olefin over a gamma alumina catalyst to form ortho-alkylphenol. The ortho-alkylphenol, free of phenol and phenol-generating ethers, is then reacted with olefin over a heterogeneous aluminum phenoxide sulfonic acid resin catalyst.

The resin-bonded aluminum phenoxide heterogeneous catalyst of the invention is a stable aluminum complex. The complex is tricoordinated but is in some cases tetra-coordinated. The degree of coordination depends on the resin used and especially on the phenoxide moiety of the catalyst. An unsubstituted phenoxide moiety tends to tetracoordinate more than a substituted phenoxide moiety.

The olefins suitable for alkylating the starting phenols of the invention include those generally unsaturated compounds of the aliphatic, alicyclic, or araliphatic series with olefinic double bonds. Thus the term "olefin" is meant to include monoolefinic alicyclic alkanes of from 2 to 12 carbon atoms, cycloalkanes of from 5 to 12 carbon atoms, and aralkanes of from 7 to 12 carbon atoms. Typical representatives are those compounds containing ethylenic unsaturation, such as ethylene, propylene, butylene, pentene, hexene, cyclopentene, cyclOhexene, and styrene. It is advantageous to use lower olefins such as the commercially available ethylene, propylene, isobutylene, and the isomeric butenes such as butene-1 or butene-2. Other examples of olefins usable in the invention are amylene, n-pent-1-ene, n-hex-1-ene, n-hept-1-ene, n-oct-1-ene, n-non-1-ene, propene, as well as these alkenes substituted by methyl, ethyl, n-propyl, isopropyl, n-butyl, isobutyl, sec-butyl, or tert-butyl in the 2, 3, or 4 positions. Other exemplary olefins are 2,3-dimethyl-n-butene, 3,3-dimethyl-n-butene, 2,5-dimethylheptene, 3,3-dimethylheptene, 2,4-dimethylheptene, 4,4-dimethylhexene, 2,5-dimethylhexene, 2,3,3-trimethylheptene, 2,3,3,4-tetramethylpentene, and the like. Similarly, alkenes having a double bond in the 2 position or 3 position in the molecule are usable. Further olefins include those branched alkenes such as obtained in the form of mixtures, by dimerizing isobutylene or n-butene or trimerizing isobutylene or n-butene or propene or tetramerizing propene. Further examples of usable olefins for the invention are ortho-methylstyrene, para-methylstyrene, 3,4-dimethylstyrene, ortho-ethylstyrene, 3,4-diethylstyrene, 2,5-diethylstyrene, ortho-isopropylstyrene, para-butylstyrene, ortho-sec-butylstyrene, ortho-tert-butylstyrene, and para-tert-butylstyrene. Preferred olefins include isobutylene, butene-1, butene-2, diisobutene, styrene, ethylene, and the like.

The process of the invention is preferably carried out in a liquid reaction medium. The medium may be in excess of one or both of the reactants or an innocuous liquid medium.

For some of the alkylation processes, the use of excess olefin (e.g. isobutylene) is highly preferred because this permits carrying out the process at a low temperature, sometimes below the melting point of the product 2,4-di-substituted phenol. As the product is formed, it remains, however, dissolved in the excess olefin. Operation at the lower temperature advantageously decreases the amount of byproducts and increases the yield.

In one embodiment, the liquid reaction medium is a hydrocarbon. Thus any of the well known hydrocarbon reaction mediums such as toluene, hexane, heptane, trimethylpentane, xylene, and the like are suitable for the invention, toluene being preferred.

The catalyst materials of the invention are referred to as heterogeneous because they are solid in nature and do not usually dissolve into otherwise homogeneous reaction mixture of a phenol (and liquid reaction medium such as toluene). Compare the homogeneously catalyzed processes wherein aluminum phenoxides are formed by the reaction of aluminum or aluminum alkyls with a phenol to form a catalyst which is generally readily dispersed in the reaction medium.

In the batch type process of the invention, the phenol to be alkylated is placed in a suitable pressure vessel, the catalyst is provided therein, and the olefinic components are then added under pressure sometimes at elevated temperature. To effect uniform distribution and assure mixing of the catalyst in the mixture, it is advantageous to agitate, stir, or shake the contents of the pressure vessel with suitable agitation means. Excess agitation which would destroy the structure or particle size of the heterogeneous catalyst is usually not helpful and is undesirable. Generally, any of the aluminum precursors and a phenol which was used to prepare a homogeneous catalyst heretofore may also be usable according to the present invention to prepare a heterogeneous catalyst for the process of the invention.

Alternatively, the heterogeneous catalyst may be provided in a packed bed through which the reactants are passed.

The ratio of olefin to phenol to be alkylated will vary depending upon the desired product, the particular catalyst chosen, and the degree of conversion and alkylation sought. If only one alkyl radical is to be introduced onto the phenol nucleus, then approximately equimolar quantities of phenol and olefin need be used although greater or lesser quantities of one may be used in some cases.

In most embodiments of the invention, it is generally preferred that the olefins and alkyl groups have at least four carbon atoms as the process is thereby accomplished more speedily. It is particularly preferred that isobutylene be used and that the mono-ortho-substituted phenol be 2-tert-butylphenol for the preparation of 2,4-di-tert-butylphenol.

The products achieved by using isobutylene, butene-1, butene-2, propene, and certain other olefins as well as appropriate reactant phenols, are commercial antioxidants which have a strong demand in the market place. In general, in a preferred embodiment of the invention, the olefin corresponds to any alkyl substituent $R_1$ or $R_2$ as given in structure I above thereby providing a more facile and speedier reaction.

The quantity of catalyst to be used depends on the activity of the particular catalyst chosen, the nature of the underlying resin of the catalyst, and the particular alkylation procedure to be carried out. In general, however, a discontinuous or batch method of alkylation can suitably be carried out with as little as 0.1% by weight to as high as 30% by weight catalyst on the basis of the weight of phenol to be alkylated. More preferably, a range of 0.5 to 10.0 percent by weight catalyst based on the weight of phenol is conveniently used. In a continuous method of operation, for example using a fixed bed, a high quantity of catalyst may be desired wherein the catalyst weight range is from 0.02 to 10 parts by weight catalyst per part by weight of phenol per hour passed therethrough. More preferably, about 0.4 to 1 part by weight catalyst per one part by weight of phenol per hour passed through the catalyst.

The alkylated product of the inventive process may be recovered by conventional means by simply decanting the liquid reaction mixture, filtering off the catalyst, or removing the fixed catalyst bed for reuse, or where desired and necessary, regeneration. In continuous operation, the catalyst and phenol to be alkylated may be pumped through the pressure reactor where an olefin is added. Alternatively, the phenol alone may be pumped through the pressure reactor where the catalyst is in a fixed bed and the olefin is added.

According to the invention, phenols alkylated in the para and at least one ortho position are obtained from the starting phenols. Thus, the products of the invention include 2,4-di-tert-butylphenol, 2,4-di-sec-butylphenol, 2,4,6-tri-tert-butylphenol, 2,4-diisopropylphenol, 2,4-dicyclohexylphenol, 2,4-di-alpha-methylbenzylphenol, 2,4,6-tricyclopentylphenol, 2-methyl-4-cyclopentylphenol, 2-ethyl-4-isopropylphenol, 2-methyl-4,6-di-tert-butylphenol, and the like.

A tremendous advantage of the present invention over homogeneously catalyzed techniques is that most of the resin-bound aluminum catalyst is reusable and is not lost as a phenol-bearing waste stream. This is a significant economical savings over the homogeneously catalyzed process. Recycle of the catalyst is easily accomplished by settling the reaction mass, decanting the liquid reaction product, and slurrying the catalyst with a suitable starting phenol for charging to a subsequent reaction. Furthermore, the use of the heterogeneous catalyst of the invention prevents problems of corrosion involved with recovery of a homogeneous aluminum catalyst. That is, it is not necessary to hydrolyze and neutralize the aluminum catalyst as in a homogeneously catalyzed process and furthermore it is not necessary to then dispose of a phenol-bearing aluminum waste stream.

Finally, the heterogeneous resin-bonded catalyst of the invention is also advantageous in lowering the overall cost of transalkylation-dealkylation procedures to recover additional products from 2,4,6-trialkylated phenols and similar by-products. The transalkylation reaction using the heterogeneous catalyst of the invention requires a lower operating temperature and is completed in less time than that required when using a homogeneous aluminum phenoxide catalyst. The temperatures usable for transalkylation with the heterogeneous catalyst of the invention are in general about 100° lower than that for the homogeneously catalyzed transalkylation reaction.

The heterogeneous catalyst of the invention include the reaction products formed by first reacting an aluminum alkyl or other aluminum compound with a solid polymeric resin to bond the aluminum to the resin followed by reaction with a phenol to form an aluminum phenoxide bonded to the solid polymeric resin. The aluminum materials usable for preparation of the heterogeneous aluminum phenoxide catalyst include aluminum phenoxides, aluminum halides, and aluminum alkyl compounds such as trimethyl aluminum, triethyl aluminum, tri-n-propyl aluminum, tri-isobutyl aluminum, and diisobutyl aluminum hydride, may be used. Also suitable are compounds such as diethyl aluminum malonate, diethyl aluminum hydride, diethyl aluminum chloride, and triphenyl aluminum. Other aluminum source compounds are also usable to react with a resin thereby bonding the aluminum to the resin. For example, diphenoxy aluminum hydroxide is usable.

The solid polymeric resins of the heterogeneous catalyst of the invention may be of the ion exchange type, the absorber type, or another type. As noted above, in the process of preparing the heterogeneous catalyst of the invention the resins are chemically reacted with aluminum compounds. The solid polymeric acidic resins usable in the heterogeneous catalyst of the invention in general include all acidic resins which have functional groups with a highly electronegative atom with a donatable hydrogen atom or other leaving group which facilitates reaction of the resin with an aluminum compound (aluminum phenylate, aluminum alkyl, aluminum phenoxide, etc.).

The resins usable for the invention are those solid polymeric resins having an acid functionality. Examples of such resins include the acidic styrene-divinylbenzene copolymer, acidic cross-linked styrene copolymer, and acidic phenolformaldehyde or benzene-formaldehyde resins having pendant acid groups. The sulfonated styrene divinylbenzene copolymer ion exchanger is highly preferred.

Examples of usable acid functionalities for the resins of the invention include the preferred sulfonic group —$SO_3H$ as well as —$PO_4H_2$, sulfinic (—$SO_2H$) and the like. The particle size of the catalyst may vary over a broad range and a typical range is from 100 to 1000 microns, more commonly 200 to 800 microns or preferably 400-500 microns. The preferred resins are of the macroreticular type, not the gelular type. An example of a commercially available preferred resin of the invention is the Dowex ® MSC-1 sulfonic acid ion exchange resins and the Rohm & Haas Amberlyst ® 15 sulfonic acid ion exchange resin.

Sulfonic acid resins are available in both wet and dry forms. They should be dried before use in the invention. Advantageously, the resins are dehydrated by conventional methods such as heating at about 100° C. under reduced pressure prior to their use as a catalyst resin. Other drying techniques may also be used. During the reaction, the catalyst is either in a suspension or a fixed bed for contacting the phenol in the presence of an olefin. Although it is not necessary to add solvents in the alkylation of the phenols, solvents which are inert under the reaction conditions may be desirably used such as for lowering the viscosity of the reaction mixture. Examples of suitable solvents are the aliphatic or cycloaliphatic hydrocarbons such as heptane, nonane, toluene, cyclohexane, decahydronaphthalene, and the like. Halohydrocarbons may also be used such as chlorohydrocarbons including 1,1,2,2-tetrachloroethane, carbon tetrachloride, dichlorobutane, methylchloride, and the like. A broad range of solvent may be added for the desired purpose. As little as one percent to as much as 1,000 percent by weight based on the amount of olefin more preferably from about 50-100 percent by weight based on the amount of olefin may desirably be used.

The alkylated phenols of the invention are suitably used as antioxidants, starting materials for pesticides, pharmaceuticals, stabilizers, other antioxidants including phosphites and numerous other uses.

The catalyst of the invention may be prepared by first loading aluminum onto a resin which has acid functional groups such as —$SO_3H$ and then providing an aluminum phenoxide or an aluminum alkyl to react with the —$SO_3H$ functional group followed by reaction with a phenol. Thereafter, this aluminum phenoxide-loaded resin may be advantageously used to catalyze the alkylation of phenols.

The addition of the aluminum to the resin may be carried out at room temperature or over a broad range of temperatures so long as the integrity of the resin is maintained. A convenient range is −20° C. to 120° C. It should be noted that many of the sulfonic acid ion exchange resins begin to degrade at as low as 120° C., more commonly as low as 150° C. Other acidic resins degrade at higher and lower temperatures. Thus, this temperature restriction, depending upon the particular resin used may also limit the temperature at which an alkylation or transalkylation reaction may be carried out.

The resin may be directly loaded with phenoxy aluminum catalyst function by reacting the resin directly with a phenoxy aluminum compound or with a phenoxy aluminum compound in an inert solvent such as hexane, benzene, or toluene. The aluminum phenoxide-type compounds are typically aluminum triphenoxides such as $Al(OC_6H_5)_3$. Also usable, however, for direct loading the phenoxide function are aluminum compounds, especially aluminum alkyls which include at least one phenoxy moiety such as di(ortho-t-butylphenoxy) ethyl aluminum: $CH_3CH_2Al(OC_6H_5C_4H_9)$.

Alternatively the resin may be first loaded with aluminum by reacting the resin with an aluminum compound that does not contain a phenoxy moiety. Such aluminum compounds include the aluminum alkyls such as triethyl aluminum, trimethyl aluminum, diethyl aluminum chloride, ethyl aluminum dichloride, diisobutyl aluminum hydride, diethyl aluminum hydride, and others. Triethyl aluminum is preferred.

Also usable are the aluminum compounds having an alkoxide function such as aluminum triethoxide, ethyl aluminum dimethoxide, diisopropoxy aluminum hydride, and others.

Typical compounds which are usable for loading the aluminum phenoxide directly onto the resin include those aluminum triphenoxides and alkyl diphenoxide aluminums such as ethyl aluminum diphenoxide, n-butyl aluminum diphenoxide, and the like. Also suitable are those dialkyl aluminum phenoxides such as diisobutyl aluminum phenoxide and similar compounds. Thus, suitable for loading aluminum onto the resin are those aluminum alkoxides such as aluminum triethoxide, aluminum tri-n-butoxide and aluminum ethoxide di-n-butoxide, aluminum triphenoxide, aluminum tris(ortho-tert-butylphenoxide).

As noted above, the aluminum may be separately loaded onto the resin and the phenoxide function provided thereafter. For example, the resin may be reacted at about room temperature with triethyl aluminum diisobutyl aluminum hydride, trimethyl aluminu, triisobutyl aluminum, or the like and thereafter reacted with a phenol or substituted phenol to provide a phenoxide function on the aluminum attached to the resin. The attachment of the phenoxides to the aluminum on a resin may simply be accomplished by adding the starting reactant phenol and forming a catalyst prior to alkylation.

According to the invention, yields of up to 91% of product phenols having 2,4-substitution are achieved, depending upon the reaction conditions, the olefin, the starting phenol, and the catalyst chosen. This is to be compared to the homogeneous catalyzed process wherein a single pass reaction was limited to about 75% yield.

In the acidic resin-bonded aluminum phenoxide heterogeneous catalyst of the invention, it is preferable to have two or three (for tetracoordination) phenoxide groups attached to the aluminum which is in turn attached to the resin. However, it is permissible to have only one phenoxide group so attached.

The phenoxide-donating phenol may be added to the aluminum-bearing resin over a broad range of temperatures so long as formation of the resin-bonded aluminum phenoxide heterogeneous acidic catalyst is accomplished. The time of exposure of the phenol to the aluminum-bearing resin may vary upon the amount of phenoxide desired and the temperature used. A suitable range for formation of the phenoxide is about −10° C. to 50° C.

The addition of the aluminum and the phenoxide-donating phenol may be accomplished at atmospheric pressure although subatmospheric and super atmospheric pressure may also be used. Conveniently, room temperature and pressure conditions are used for formation of the catalyst with aluminum alkyls.

The alkylation reaction of the invention may be carried out over a broad of temperatures depending upon the heterogeneous catalyst used, the phenol to be alkylated, and the olefin used for alkylation. The temperature should be high enough to accomplish the alkylation of the phenol at a reasonable rate and low enough not to destroy the formed product, catalyst, or reactants prior to formation of the desired products. The temperature also varies depending upon the olefin used for the alkylation. For example, isobutylene is one of the easiest alkylation olefins because of its structure. A suitable range of reaction temperatures for alkylating starting phenols with olefins in the presence of the heterogeneous catalyst of the invention is about 50° to 150° C. and a preferred range is about 70° to 120° C.

A preferred embodiment of the invention is the production of 2,4-di-tert-butylphenol using an acidic styrene divinylbenzene resin having attached thereto an aluminum diphenoxide catalyst. This reaction, carried out at about 90 to 100° C, produces yields as high as 91% 2,4-di-tert-butylphenol. Similar results may be achieved using other starting olefins and other starting phenols with this catalyst and related catalysts of the invention. Another desirable product of the invention having 2,4-substitution is the product 2,4-di-sec-butylphenol which is useful as an intermediate for a herbicide or pesticide. This is conveniently formed from butene-2 olefin and phenol starting material or a mixture of phenol and para-sec-butylphenol.

Advantageously, the heterogeneous catalyst of the invention may be used in a cyclical or continuous process. In a cyclical mode of operation, the styrene-divinylbenzene sulfonic acid resin having aluminum phenoxide structure was used in six subsequent recycles of starting phenol without significant loss of catalyst activity, achieving yields in excess of 75% in each case.

The catalyst of the invention may conveniently be described as having the structure (II):

(Resin—A—)$_m$ Al (—OC$_6$R$_5$)$_n$     (II)

The Resin is a solid polymeric acidic resin; m is 1 or 2; n is 2 or 3; the R are independently selected from H, alkyl, cycloalkyl, or aralkyl; and A is an acid function residue. For example the residue of —SO$_3$H is —SO$_3$—. Preferably, the alkyl are from 1-20 carbon atoms, the cycloalkyl are from 5-12 carbon atoms, and the aralkyl are from 7-12 carbon atoms. The Resin is preferably acidic styrene divinylbenzene polymeric resin of the macroreticular type. Also preferably, A is preferably —SO$_3$—, —PO$_4$H—, —SO$_2$—, most preferably —SO$_3$—. It should be understood that some of the aluminum atoms bonded to the functional group residues (e.g. —SO$_3$—) of the resin may be twice bonded. It is found, however, from the amount of phenoxide added to the aluminum that most of the aluminum atoms are bonded only once through a single functional group.

Ordinarily, with the acidic resin heterogeneous catalyst, some pendant functional groups (e.g. —SO$_3$H) remain unreacted and can contribute as a catalyst species, to the alkylation of the reactant phenol primarily in its para position. Also a proton of the unreacted functional group may add to the olefin, e.g. isobutylene, to provide a carbonium, e.g. tert-butyl, ion for reaction.

The use of the resins of the invention to form a heterogeneous catalyst for alkylation of phenols is highly desirable so as to provide an easily separable catalyst from the liquid reaction mixture containing alkylated product thereby avoiding the expensive hydrolysis procedure used with homogeneous catalyst systems. Thus, aluminum phenoxides can be chemically bonded to solid polymeric resins having acidic functional groups and used as a heterogeneous catalyst in the reaction of phenols and olefins. The catalyst life and the rate of aluminum loss varies depending upon the particular resin and the reaction conditions but in general, the heterogeneous catalyst of the invention are far superior in reducing the cost attributable to the loss of catalytic aluminum.

The yields for the processes of the invention using the heterogeneous catalyst are very similar to those observed for the homogeneous route but the process is, overall, much more economical. The reaction rates for heteregeneous catalyst reactions are sometimes slightly lower than the rates for homogeneous reactions with equivalent amounts of aluminum. However, this does not seriously detract from the significant savings available by the decrease in phenol-contaminated aluminum waste. The present heterogeneously catalyzed process of the invention provides as much as an order of magnitude decrease in the amount of aluminum waste stream and greatly reduces the distillation and energy requirements by improving conversions per pass. The styrene-divinylbenzene sulfonic acid resin is preferred for some embodiments of the invention including the production of 2,4-di-lower-alkylphenols.

In each homogeneously catalyzed alkylation of a phenol using the heterogeneous catalyst of the invention, the amount of aluminum used as catalyst and lost is about 0.5 weight percent of the total reaction mixture or about 0.7 weight percent of the 2,4-di-substituted phenol product. In experiments using the heterogeneous catalyst of the invention, as much as about 0.5 weight percent of the aluminum may be lost in a first heterogeneously catalyzed alkylation, but the rate of loss drops off precipitously (to nil) in subsequent alkylations using the same aluminum/resin heterogeneous catalyst while the catalyst remains active.

In another embodiment of the invention, the heterogeneous catalyst is useful in the transalkylation of polysubstituted phenols such as 2,4,6-tri-tert-butylphenol and the like. These polysubstituted phenols have at least two independently selected alkyl, cycloalkyl, or aralkyl groups. Included are 2-tert-butyl-4-methyl-6-sec-butylphenol; 2-methyl-6-tert-butylphenol; 2,6-di-cyclohexylphenol; 2,4,6-tri-cyclopentylphenol; 2,4,6-tribenzylphenol, 2,6-dibenzyl-4-tert-butylphenol, 2,6-di-octylphenol, 2-octyl-6-methylphenol, and others. According to the invention, the transalkylation is carried out by heating the polysubstituted phenol in the presence of the compound phenol at a temperature high enough to cause transalkylation of the polysubstituted phenol but not so high as to degrade the integrity of the resin in the heterogeneous catalyst. A suitable range is about 90°–150° C., more preferably 100°–120° C. A preferred embodiment of the invention is the transalkylation of a bottom stream from the production of 2,6-dialkylphenols such as 2,6-di-tert-butylphenol. In these preparations, the main by-product in a bottom stream is 2,4,6-tri-substituted phenol such as 2,4,6-tri-tert-butylphenol. This is a generally less usable product which is advantageously converted to a phenol having less substitution which is more usable or saleable.

The aluminum alkyls usable with the invention to bond aluminum to the resin of the heterogeneous catalyst are any of various compounds including not only those having alkyl substituents per se but also those having, for example, halo substituents such as the compound diethyl aluminum chloride and the like. Furthermore, various other salts which may be considered "aluminum alkyls" are included within this aspect of the invention so long as the aluminum may be loaded onto the resin base of the heterogeneous catalyst. Exemplary aluminum alkyls are triethylaluminum, diisobutylaluminum hydride, and the like.

The following phenols are also usable to form the catalyst of the invention by reaction with the aluminum which has been loaded onto the resin base of the heterogeneous catalyst: phenol, ortho-tert-butylphenol, 2,4-di-tert-butylphenol, ortho-sec-butylphenol, ortho-isopropylphenol, 2,6-di-sec-butylphenol, 2,6-di-sec-butylphenol, para-n-phenol, para-isopropylphenol, para-cyclohexylphenol, ortho-cyclopentylcresol, and the like.

A better understanding of the invention may be had by a review of the following examples:

EXAMPLE 1

A heterogeneous catalytic reaction was carried out according to the process of the invention by reaction 69.5 grams of dry Dowex ® MSC-1H styrene divinylbenzene resin with a stoichiometric excess of aluminum triphenoxide. This formed a catalyst having two phenoxide groups to function as catalyst for the alkylation reaction. The resin catalyst, about 200 grams (wet), was loaded into a stainless steel autoclave and an alkyation reaction was carried out at about 95° C. with 45 grams phenol and 538 grams isobutylene at a pressure of about 250 psig. After two hours the purity of 2,4-di-tert-butylphenol was 78.7% and the yield based on reacted phenol was 91%. Both ortho-tert-butylphenol and para-tert-butylphenol were produced as intermediates (as evidenced by sampling during the reaction) and 2,4,6-tri-tert-butylphenol was a by-product.

The process was repeated with the same catalyst after filtering solids from the product-containing decant and returning such solids (aluminum containing) to the reactor. In a subsequent recycle, the yields of 2,4-di-tert-butylphenol on reacted phenol was 88.6%.

The total combined loss of aluminum for the two runs was a negligible amount as measured by ethylenediaminetetraacetic acid The above example compares very advantageously to the homogeneous reaction wherein four full portions of aluminum (of about the same quantity used for one reaction here) would be lost as contaminated waste for landfill. This loss is not only a loss of the value of the aluminum but also a loss of the additional costs of preparing separate homogeneous catalyst butenes, treating the product decant to remove the aluminum, disposing of the phenol-bearing waste by landfill, and monitoring the landfill. The homogeneous catalyst reaction mixture must be first acidified so that the product remains dissolved in the decant liquid while the catalyst is taken off with an acid phase cut, neutralized with base to protect the distillation/separation equipment and recovered. With the heterogeneous catalyst of the invention, the solid catalyst is easily separated by settling and optionally filtering where necessary.

When the heterogeneous catalyst resin of the invention is used in a packed bed, catalyst losses, especially from elutriation and agitation damage to the resin particles, is diminished and the catalyst utilization may be further increased (and disposal costs further decreased).

EXAMPLE 2

A column bottom stream from the distillation of crude 2,6-di-tert-butylphenol was reacted with an equal portion of phenol at about 100° C. in the presence of an aluminum phenoxide divinylbenzene styrene sulfonic acid heterogeneous catalyst. Using agitation, the reaction mixture was carried out at a much lower temperature than required for the conventional homogeneous catalyst dealkylation (usually about 230° C.). The stream contained the following components: 63% 2,4,6-tri-tert-butylphenol, 7% 2,6-di-tert-butylphenol, 7% 2,4-di-tert-butylphenol, 6% 2,5-di-tert-butylphenol, 7% ethylene-bis(2,6-di-tert-butylphenol), 1% 1,1,3,3-tetramethylbutylphenol, and 9% heavier components. The primary reactant 2,4,6-tri-tert-butylphenol and the phenol reactant were transalkylated in the presence of the heterogeneous catalyst to the intermediate 2,4-di-tert-butylphenol and eventually to the primary product para-tert-butylphenol and 3 moles of isobutylene for each mole of 2,4,6-tri-tert-butylphenol.

Similar transalkylation processes can be carried out at various temperatures, pressures, and reaction conditions using a suitable heterogeneous catalyst of the invention.

Certain aspects of the invention such as temperature, time of reaction, resin for the heterogeneous catalyst, alkoxide function on the aluminum heterogeneous catalyst, and other factors may be varied without departing from the scope or spirit of the invention which is defined by the appended claims.

We claim:

1. A process for producing 2,4-di-substituted phenols comprising reacting an ol-efin and a phenol of structure I:

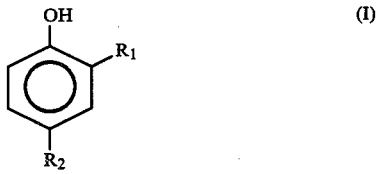

wherein one of $R_1$ and $R_2$ is H and the other is independently selected from the group consisting of H, alkyl of from 1-12 carbon atoms, cycloalkyl of from 5-12 carbon atoms, and aralkyl of from 7-12 carbon atoms; said reacting being carried out in the presence of a heterogeneous catalyst comprising an aluminum phenoxide bonded to a solid polymeric resin having acidic functional groups; and forming as the major product 2,4-di-substituted phenol.

2. The process of claim 1 wherein said resin is a styrene-divinylbenzene resin.

3. The process of claim 1 wherein said acidic resin has sulfonic acid functional groups.

4. The process of claim 2 wherein said styrene-divinylbenzene resin has sulfonic acid functional groups.

5. The process of claim 1 wherein $R_1$ and $R_2$ are both H.

6. The process of claim 1 wherein $R_2$ is H and $R_1$ is tert-butyl.

7. The process of claim 1 wherein $R_2$ is H and $R_1$ is sec-butyl.

8. The process of claim 1 wherein $R_2$ is H and $R_1$ is isopropyl.

9. The process of claim 1 wherein one of $R_1$ and $R_2$ is methyl.

10. The process of claim 1 wherein said olefin has 2-20 carbon atoms.

11. The process of claim 10 wherein said olefin is isobutylene.

12. The process of claim 11 wherein $R_1$ and $R_2$ are both H and 2,4-di-tert-butylphenol is formed as the major product.

13. The process of claim 10 wherein said olefin is butene-2.

14. The process of claim 13 wherein $R_1$ and $R_2$ are H and 2,4-di-sec-butylphenol is formed as the major product.

15. The process of claim 10 wherein said olefin is propylene.

16. The process of claim 1 wherein said phenol is a mixture of para-tert-butylphenol and the compound phenol; said olefin is isobutylene; and 2,4-di-tert-butylphenol is formed as the major product.

17. The process of claim 1 wherein said heterogeneous catalyst is formed by reacting an aluminum phenoxide and a solid polymeric resin having sulfonic acid functional groups.

18. The process of claim 17 wherein said aluminum phenoxide is an aluminum triphenoxide.

19. The process of claim 1 further comprising separating said heterogeneous catalyst from the reaction mixture.

20. The process of claim 19 wherein said separating comprises simply decanting liquid reaction mixture.

21. The process of claim 20 further comprising filtering the decant and recovering additional heterogeneous catalyst.

22. The process of claim 19 wherein said heterogeneous catalyst is recovered and used in the alkylation of a phenol with an olefin.

23. The process of claim 1 wherein said heterogeneous catalyst is contained in a fixed bed for reacting said phenol and said olefin.

24. A process for the transalkylation of polysubstituted phenols, said process comprising reacting the compound phenol ($C_6H_5OH$) and a poly-alkyl, -cycloalkyl or -aralkyl phenol at a temperature of about 90°-150° C. in the presence of a heterogenous catalyst comprising an aluminum phenoxide bonded to a solid polymeric resin through the residue of acidic functional groups and forming a phenol less substituted than said polysubstituted phenol.

25. The process of claim 24 wherein said polysubstituted phenol is a mixture of phenols comprising primarily 2,4,6-tri-substituted phenol.

26. The process of claim 25 wherein said 2,4,6-tri-substituted phenol is 2,4,6-tri-tert-butylphenol and said olefin formed is isobutylene.

27. A two stage process for producing 2,4-di-substituted phenols comprising:
(a) reacting an olefin and phenol in the presence of an aluminum-containing catalyst to form mono-ortho-substituted phenol intermediate; and
(b) reacting said mono-ortho-substituted phenol intermediate and an olefin in the presence of a heterogeneous catalyst comprising an aluminum phenoxide bonded through aluminum to the residue of acidic functional groups of a solid polymeric, resin thereby producing said 2,4-di-substituted phenol and minimizing the formation of tri-substituted phenol.

28. The two stage process of claim 27 wherein stage (b) is carried out with said heterogeneous catalyst in a fixed bed.

29. The two stage process of claim 27 wherein the olefin in both stages is isobutylene so as to form as the primary product 2,4-di-tert-butylphenol.

30. The two stage process of claim 27 wherein said aluminum-containing catalyst of stage (a) is gamma alumina.

31. The two stage process of claim 27 wherein the olefin in both stages is butene-1 or butene-2 so as to form as the primary product di-ortho-sec-butylphenol.

32. The process of claim 27 wherein step (b) is carried out at about 50° C. to 150° C. and 20–5000 psig.

33. The process of claim 24 wherein said polysubstituted phenol is substituted with 2–5 groups independently selected from the group consisting of alkyl of from 1–12 carbon atoms, cycloalkyl of from 5–12 carbon atoms and aralkyl of from 7–12 carbon atoms.

* * * * *

UNITED STATES PATENT AND TRADEMARK OFFICE
CERTIFICATE OF CORRECTION

PATENT NO. : 4,628,127
DATED : DECEMBER 9, 1986
INVENTOR(S) : Silas W. Holmes et al.

It is certified that error appears in the above-identified patent and that said Letters Patent is hereby corrected as shown below:

Column 10, line 61, reads "acid" and should read --acid.--.
Column 11, line 49, reads "ol-efin" and should read --olefin--.

Signed and Sealed this

Seventh Day of April, 1987

Attest:

DONALD J. QUIGG

Attesting Officer

Commissioner of Patents and Trademarks